US009116609B2

(12) United States Patent
Bocirnea

(10) Patent No.: US 9,116,609 B2
(45) Date of Patent: Aug. 25, 2015

(54) METHODS, APPARATUSES AND COMPUTER PROGRAM PRODUCTS FOR GENERATING REGIONS OF INTEREST USING GESTURES VIA A USER INTERFACE

(75) Inventor: Radu Catalin Bocirnea, New Westminster (CA)

(73) Assignee: McKesson Financial Holdings, Hamilton (BM)

( * ) Notice: Subject to any disclaimer, the term of this patent is extended or adjusted under 35 U.S.C. 154(b) by 1163 days.

(21) Appl. No.: 13/075,626

(22) Filed: Mar. 30, 2011

(65) Prior Publication Data

US 2012/0254747 A1  Oct. 4, 2012

(51) Int. Cl.
*G06F 3/0484* (2013.01)
*G06F 3/0488* (2013.01)
*G06F 19/00* (2011.01)

(52) U.S. Cl.
CPC .......... *G06F 3/04845* (2013.01); *G06F 3/0488* (2013.01); *G06F 19/321* (2013.01); *G06F 19/3406* (2013.01)

(58) Field of Classification Search
CPC ........ A61B 6/465; A61B 6/469; A61B 8/467; A61B 6/461; G06T 2207/20104
USPC ......................................... 715/233, 852, 863
See application file for complete search history.

(56) References Cited

U.S. PATENT DOCUMENTS

| 8,175,364 | B2* | 5/2012 | Goto et al. ..................... 382/131 |
| 2007/0255136 | A1* | 11/2007 | Kristofferson et al. ....... 600/437 |
| 2009/0116718 | A1* | 5/2009 | Goto et al. ..................... 382/131 |
| 2010/0123714 | A1* | 5/2010 | Langeland et al. ........... 345/419 |
| 2010/0298701 | A1* | 11/2010 | Shin .............................. 600/437 |
| 2012/0144345 | A1* | 6/2012 | Munter et al. ................ 715/863 |

\* cited by examiner

*Primary Examiner* — Namitha Pillai
(74) *Attorney, Agent, or Firm* — Alston & Bird LLP

(57) ABSTRACT

An apparatus is provided for generating a region(s) of interest for a medical image(s). The apparatus includes at least one memory and at least one processor configured to receive an indication of one or more touches at corresponding locations on a touch enabled display. The respective touches define a touch point at the corresponding location. The processor is further configured to generate one or more regions of interest associated with areas of a medical image(s) responsive to receipt of the indications. A location of respective regions of interest corresponds to locations of touch points. The processor is further configured to define a diameter of regions of interest based on a width/pressure of the touch points and define the regions of interest to include a disc including a contour(s). The regions of interest correspond to an area for annotating the medical image(s). Corresponding computer program products and methods are also provided.

24 Claims, 10 Drawing Sheets

METHODS, APPARATUSES AND COMPUTER PROGRAM PRODUCTS FOR GENERATING REGIONS OF INTEREST USING GESTURES VIA A USER INTERFACE

TECHNOLOGICAL FIELD

Embodiments of the invention relate generally to user interface technology and, more particularly, to a method, apparatus, and computer program product for providing a user a friendly and efficient manner in which to generate one or more regions of interest via a user interface.

BACKGROUND

Currently, medical images may be utilized for clinical purposes for diagnosis or examination of patients, for example. In this regard, the medical images may be displayed by medical viewers for analysis, editing or annotation of relevant medical data associated with the medical images. For instance, a health care professional such as, for example, a physician may utilize a medical viewer to annotate medical images by including some text describing the medical images, including arrow annotations pointing to relevant sections of the medical images, adding measurement data to the medical images and/or including other desirable data in association with the medical images.

At present, existing medical viewers typically involve annotating medical images by interacting with control points associated with the medical viewer. However, existing medical viewers are not typically amenable to touch-based interaction for annotation of medical images.

In view of the foregoing, it may be desirable to provide an alternative mechanism in which to efficiently and reliably enable annotation of one or more medical images via a user interface by utilizing touch based interaction.

BRIEF SUMMARY

A method, apparatus and computer program product are therefore provided for providing a simple and intuitive mechanism of generating one or more free-form annotations (e.g., closed curve annotations) for defining one or more regions of interest based in part on one or more touch based gestures.

In this regard, an example embodiment may provide a mechanism for efficient creation, modification and deletion of regions of interest associated with corresponding areas of medical images via touch based interaction of a touch enabled device. The regions of interest of the example embodiments may correspond to areas of a medical image(s) that may be of interest to a user. In this manner, the regions of interest may be used to identify a feature(s) associated with a corresponding area(s) of a medical image(s).

In an example embodiment, a region of interest(s) may be generated in response to an indication of a detection of touches of one or more fingers at a touch enabled device. In this regard, the detection of the touches may trigger generation of one or more corresponding regions of interest having one or more contours defined by a virtual elastic band surrounding a virtual disc of a diameter located at a contact point of each of the touches on the touch enabled device (e.g., display). An example embodiment may modify the generated region of interests in response to a detection of one or more of the contours being overlapped when one or more fingers are moved across one or more of the contours of the generated region of interests via a touch enabled device.

According to an example embodiment, modifications of a generated region(s) of interest may include, but are not limited to, expansion, removal, deletion, disjoining or merging of portions of a generated region(s) of interest and/or the like.

In one example embodiment, a method for generating one or more regions of interest for one or more corresponding medical images is provided. The method may include receiving an indication of one or more touches at a corresponding one or more locations on a touch enabled display. The respective touches define a touch point at the corresponding location. The method may further include generating one or more regions of interest associated with one or more areas of at least one medical image in response to receipt of the one or more indications. A location of respective regions of interest corresponds to the location of respective one or more touch points. The method may further include defining a diameter of respective regions of interest based in part on a width or an amount of pressure of the corresponding touch points and defining each of the regions of interest to include at least one disc including one or more contours. The respective regions of interest correspond to an area for annotating the medical image.

In another example embodiment, an apparatus for generating one or more regions of interest for one or more corresponding medical images is provided. The apparatus may include at least one memory and at least one processor configured to cause the apparatus to receive an indication of one or more touches at a corresponding one or more locations on a touch enabled display. The respective touches define a touch point at the corresponding location. The processor may further cause the apparatus to generate one or more regions of interest associated with one or more areas of at least one medical image in response to receipt of the one or more indications. A location of respective regions of interest corresponds to the location of respective one or more touch points. The processor may further cause the apparatus to define a diameter of respective regions of interest based in part on a width or an amount of pressure of the corresponding touch points and define each of the regions of interest to include at least one disc including one or more contours. The respective regions of interest correspond to an area for annotating the medical image.

In another example embodiment, a computer program product for generating one or more regions of interest for one or more corresponding medical images is provided. The computer program product includes at least one computer-readable storage medium having computer-executable program code instructions stored therein. The computer-executable program code instructions may include program code instructions configured to cause receipt of an indication of one or more touches at a corresponding one or more locations on a touch enabled display. The respective touches define a touch point at the corresponding location. The program code instructions may also be configured to generate one or more regions of interest associated with one or more areas of at least one medical image in response to receipt of the one or more indications. A location of respective regions of interest corresponds to the location of respective one or more touch points. The program code instructions may also be configured to define a diameter of respective regions of interest based in part on a width or an amount of pressure of the corresponding touch points and define each of the regions of interest to include at least one disc including one or more contours. The respective regions of interest correspond to an area for annotating the medical image.

Embodiments of the invention may provide a better user experience given the ease and efficiency in generating one or more regions of interest for medical images via a user interface. As a result, device users may enjoy improved capabilities with respect to annotating medical images.

BRIEF DESCRIPTION OF THE SEVERAL VIEWS OF THE DRAWINGS

Figure 1:
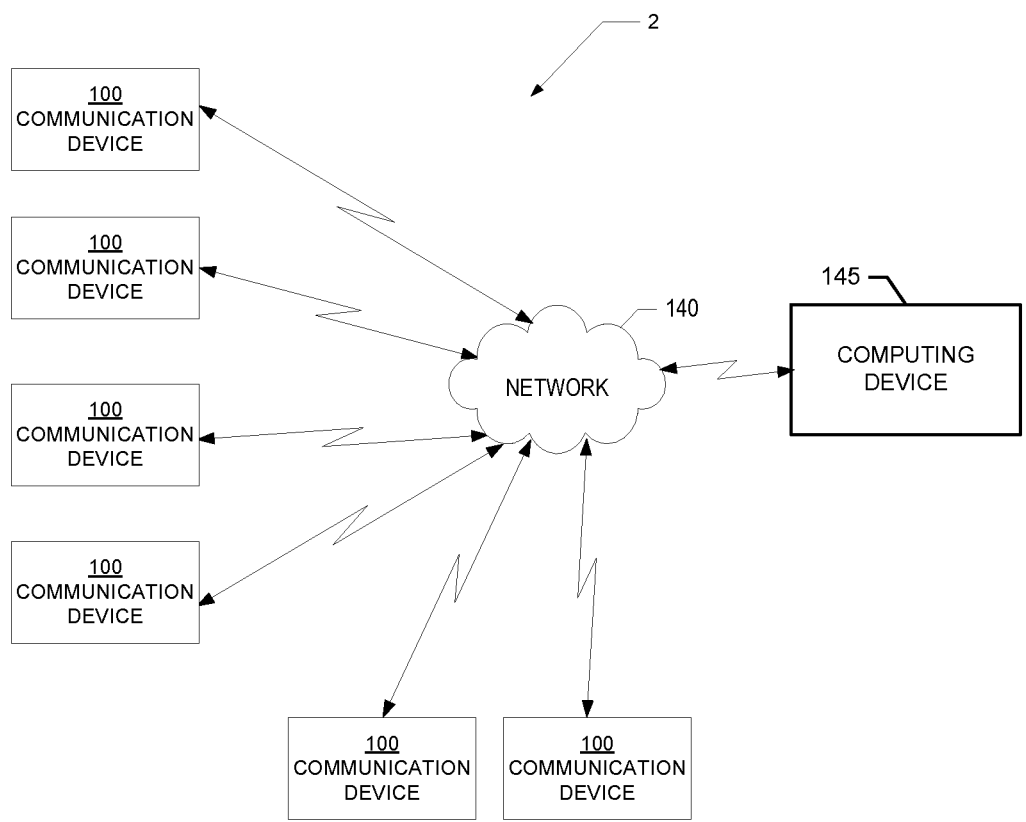
Figure 2:
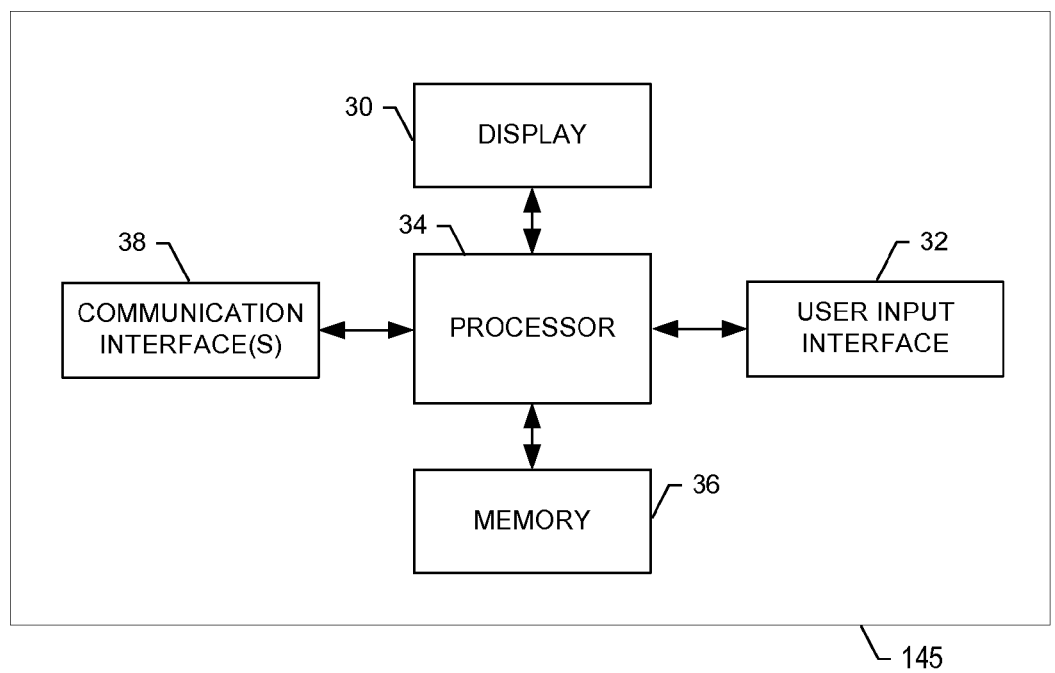
Figure 3:
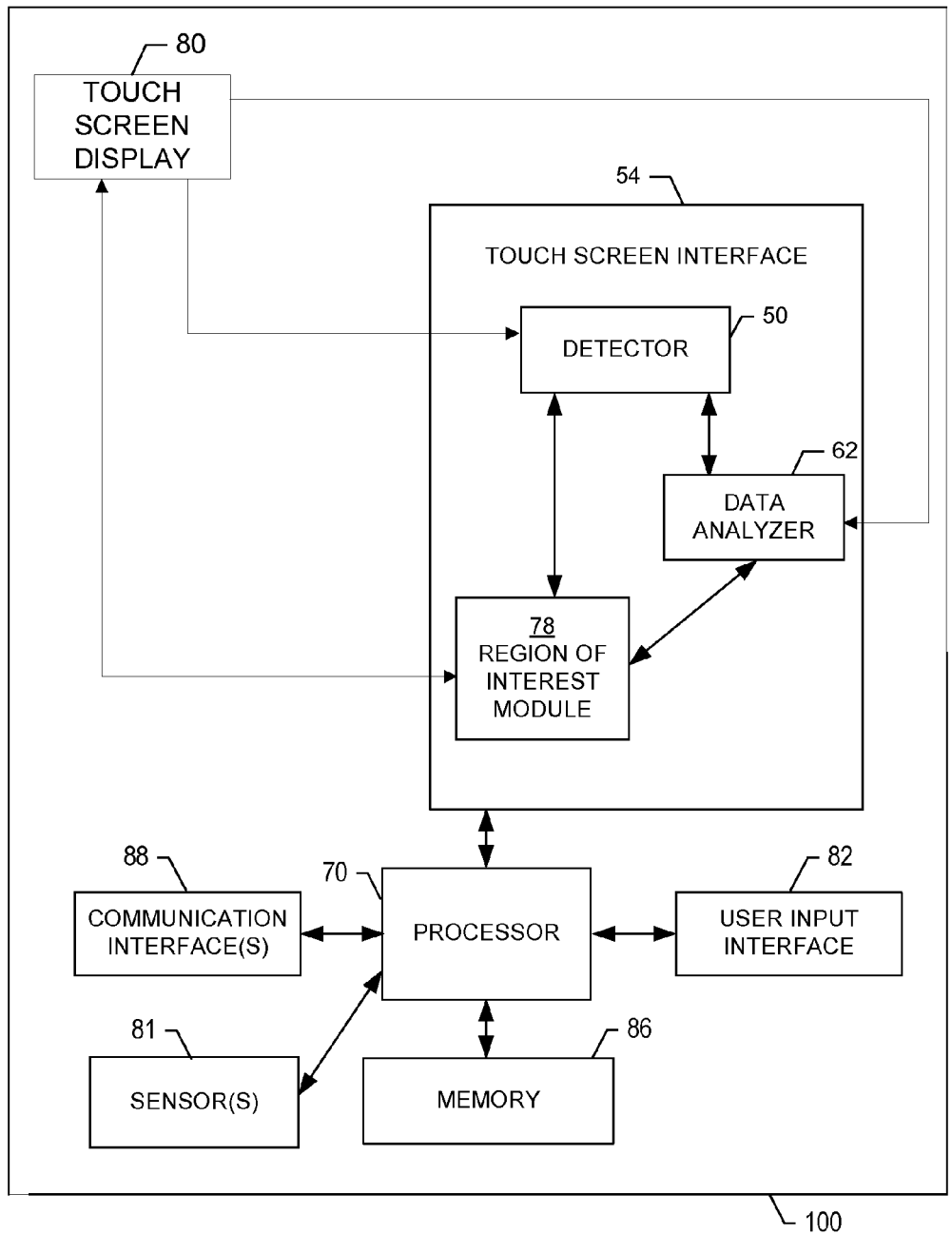
Figure 4:
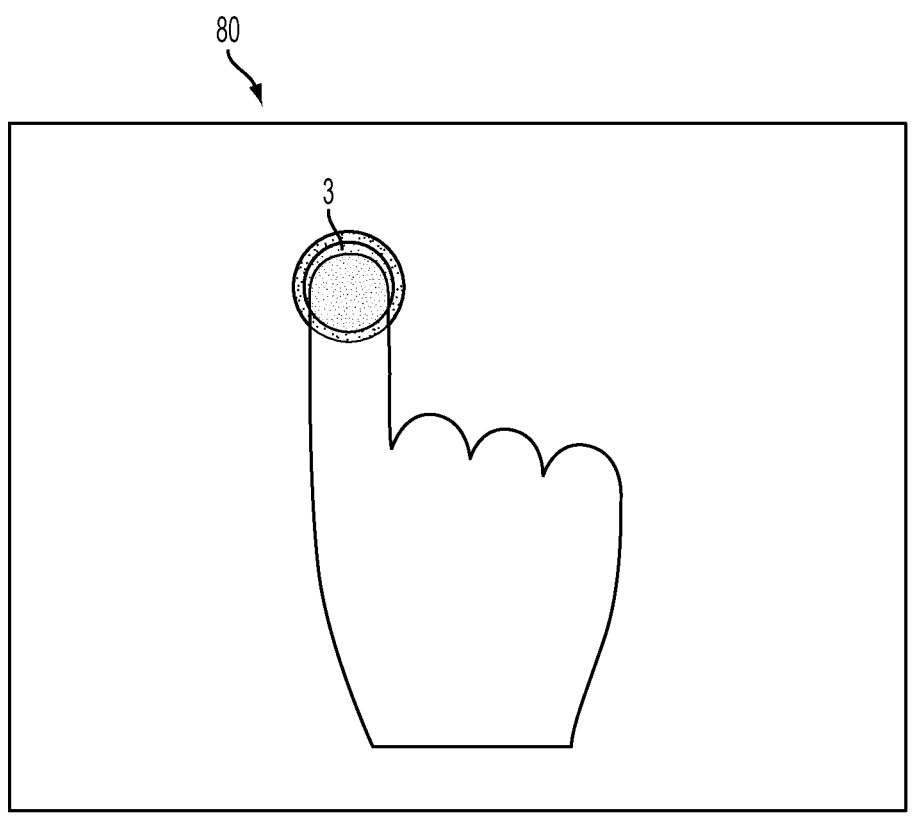
Figure 5:
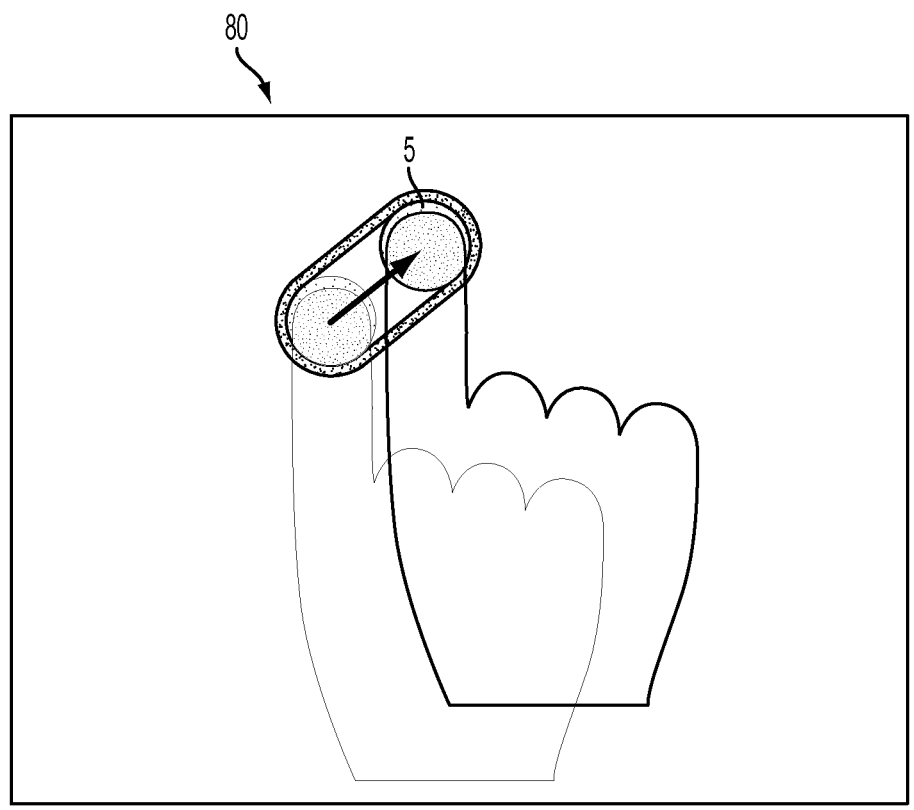
Figure 6:
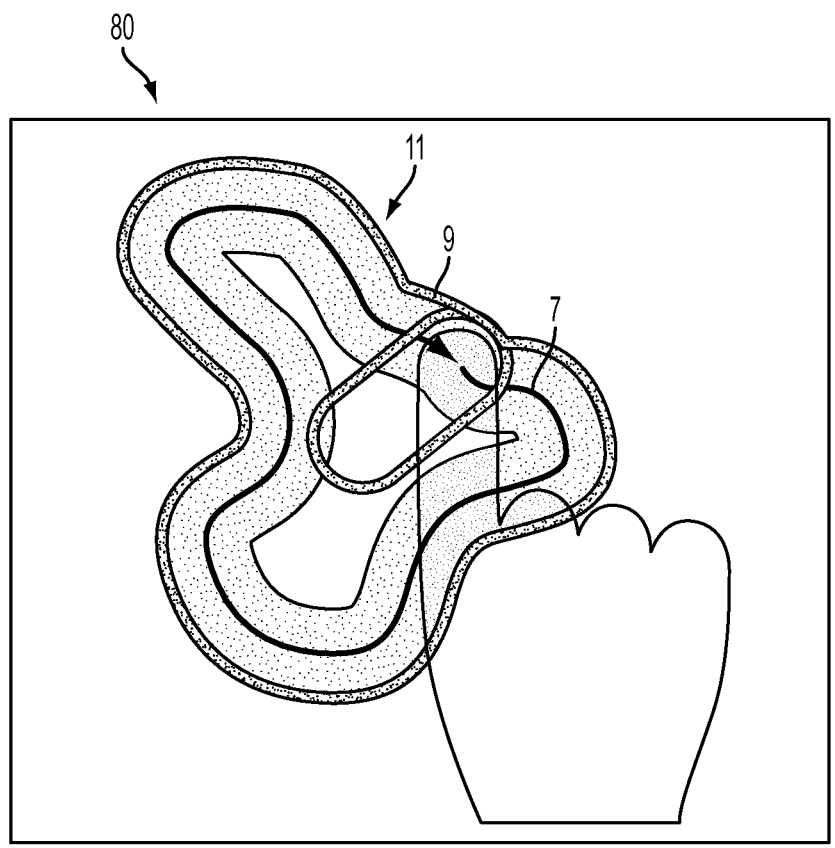
Figure 7:
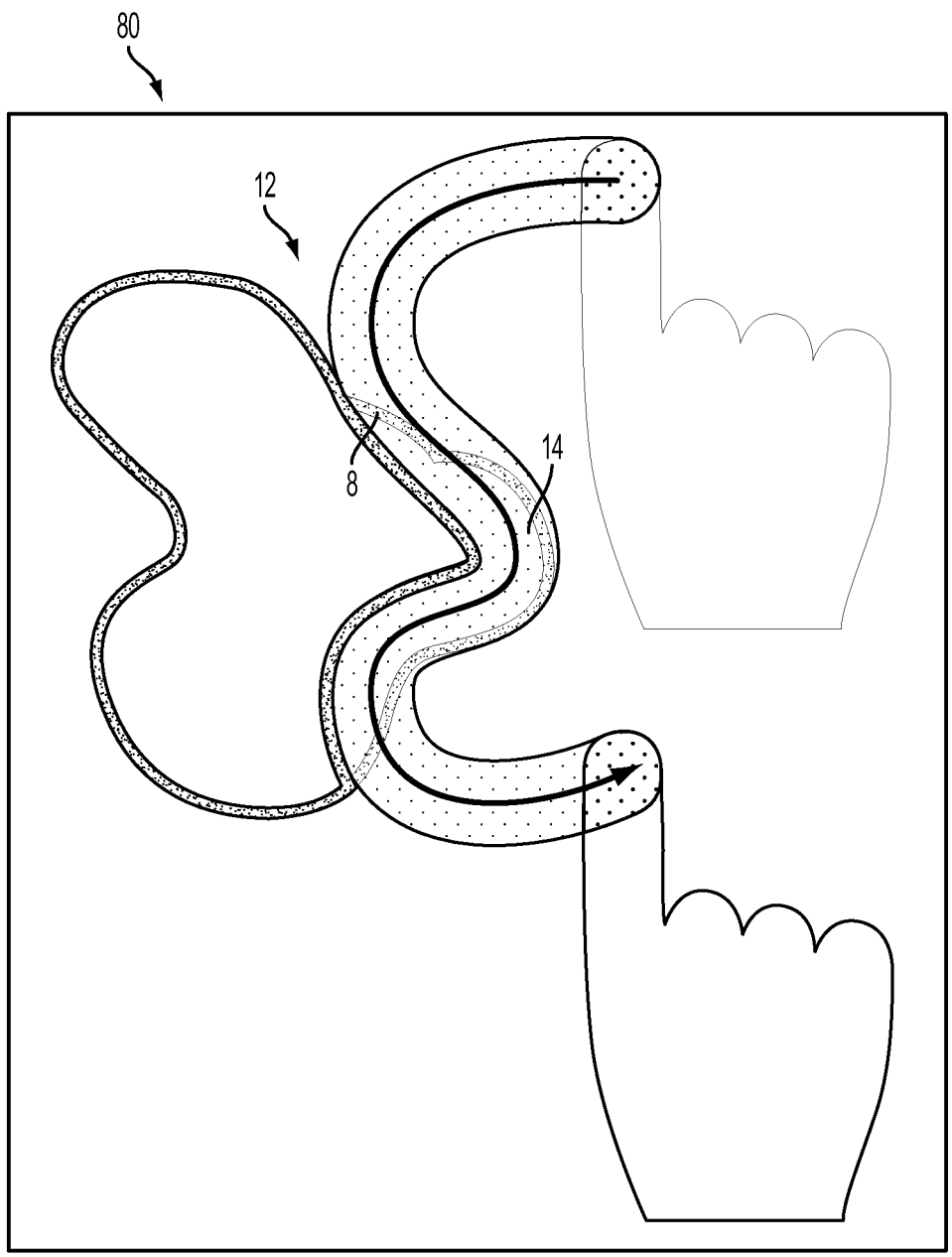
Figure 8:
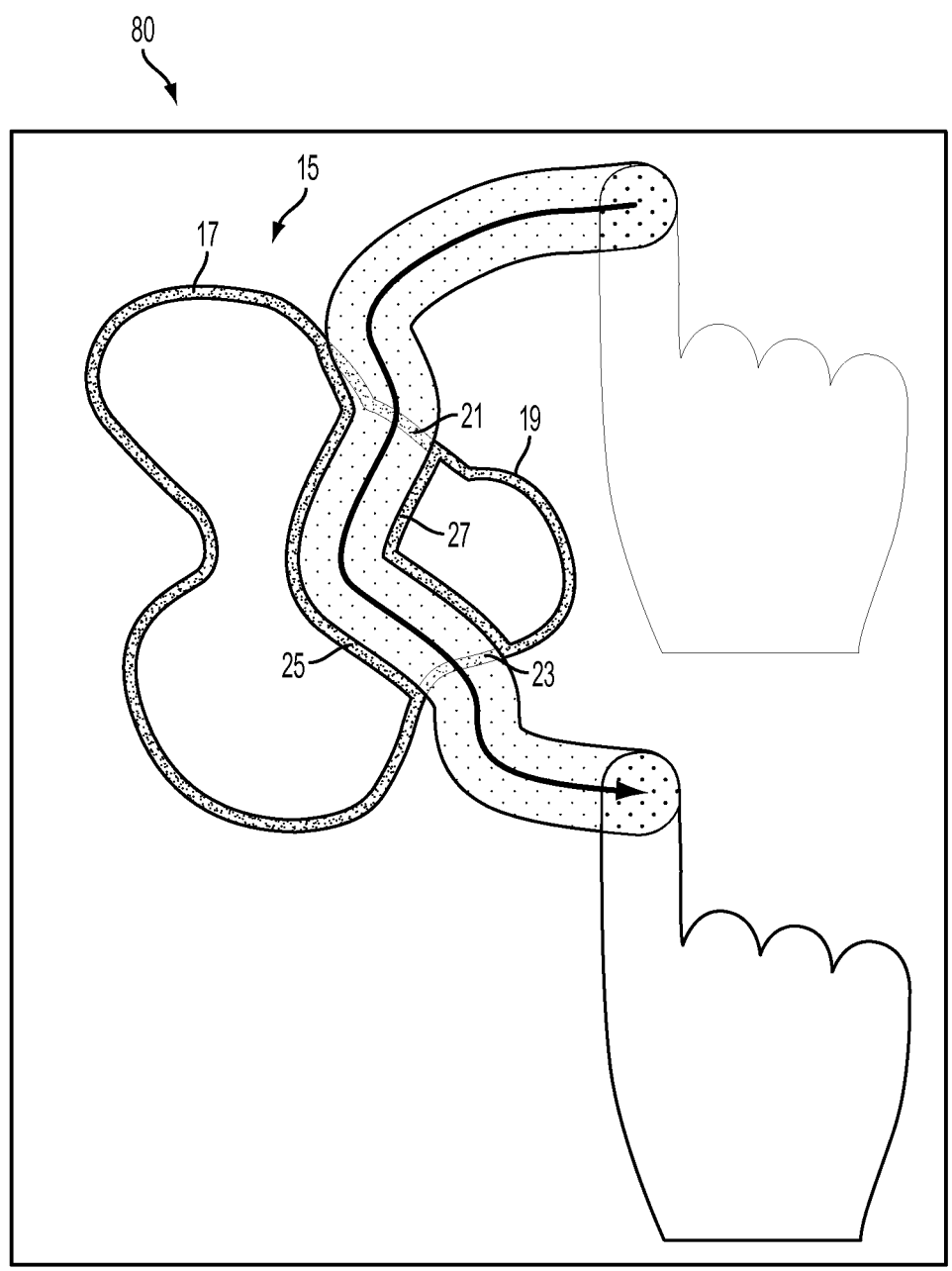
Figure 9:
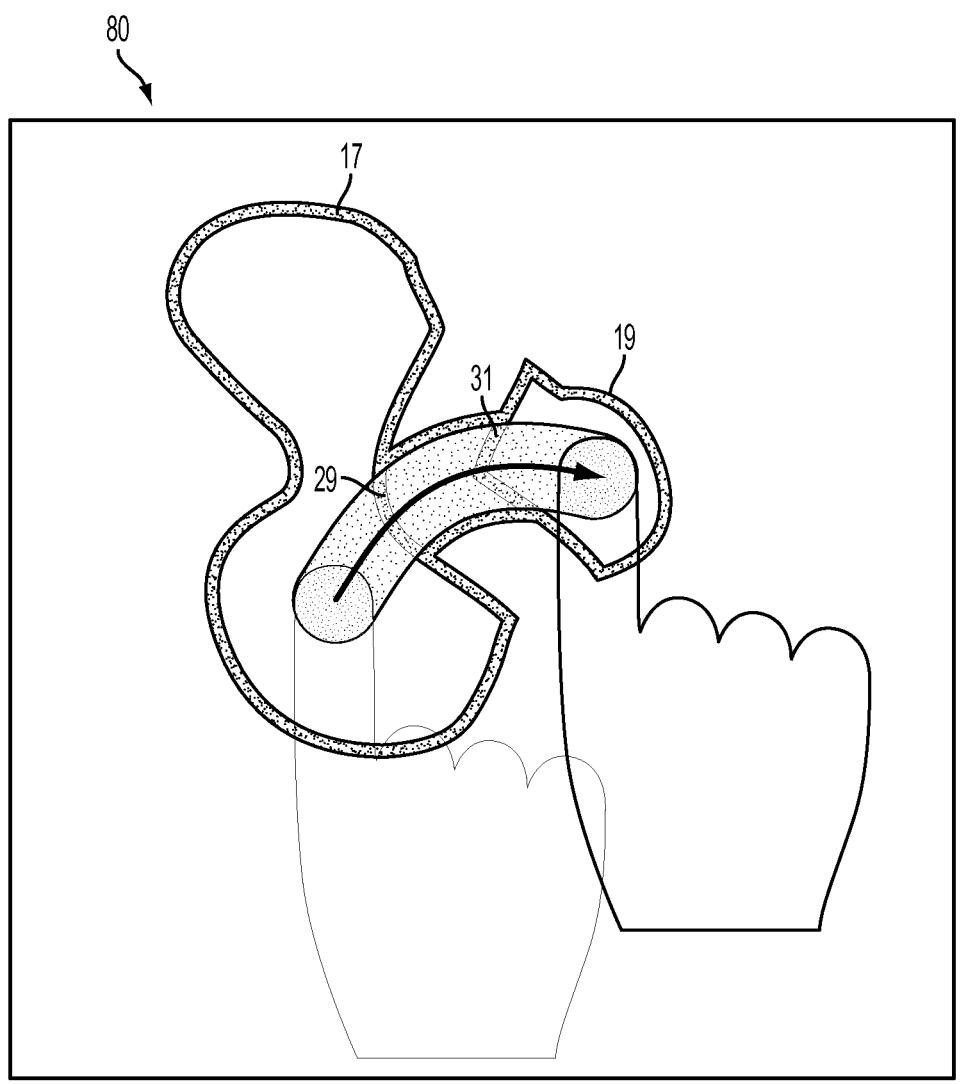
Figure 10:
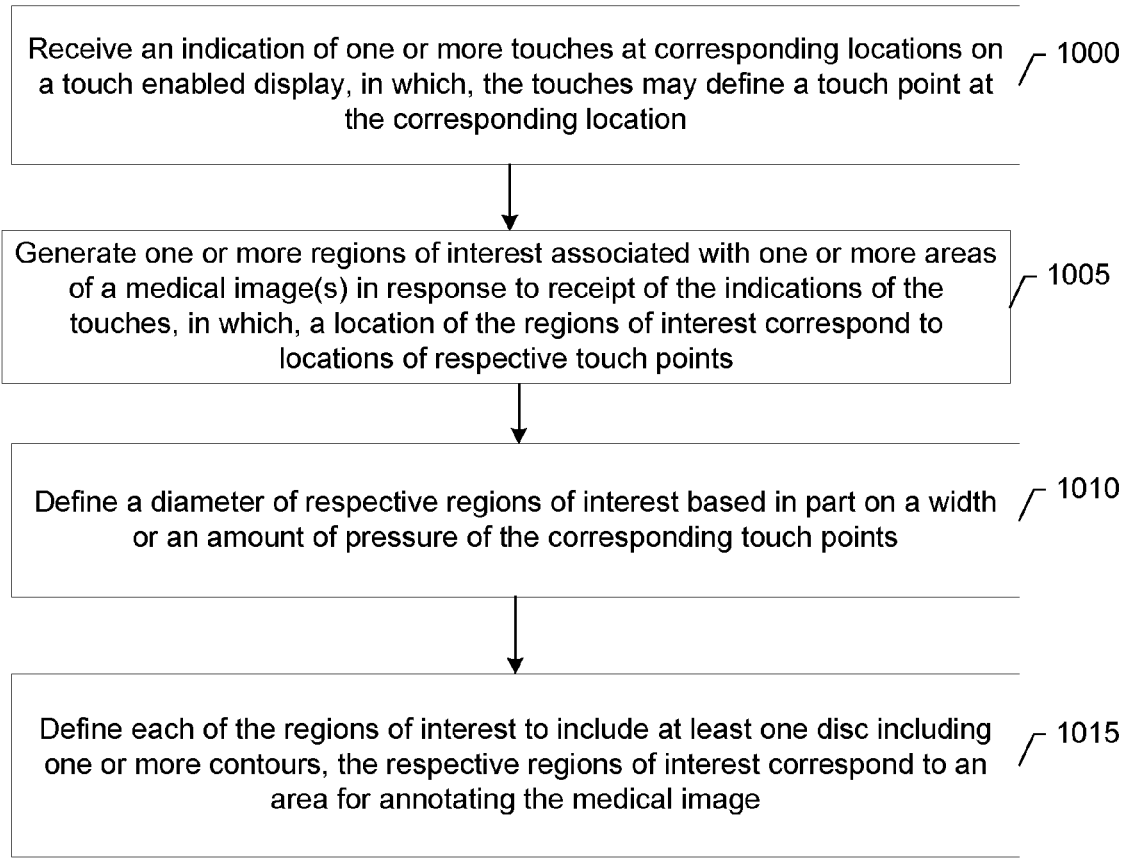

Having thus described the invention in general terms, reference will now be made to the accompanying drawings, which are not necessarily drawn to scale, and wherein:

FIG. 1 is a schematic block diagram of a system according to an example embodiment of the invention;

FIG. 2 is a schematic block diagram of a computing device according to an example embodiment of the invention;

FIG. 3 is a schematic block diagram of a communication device according to an example embodiment of the invention;

FIG. 4. is a diagram illustrating generation of a region of interest according to an example embodiment of the invention;

FIGS. 5 & 6 are diagrams illustrating expansion of a generated region of interest according to an example embodiment of the invention;

FIG. 7 is a diagram illustrating shrinking of a generated region of interest according to an example embodiment of the invention;

FIG. 8 is a diagram illustrating disjoining of a generated region of interest according to an example embodiment of the invention;

FIG. 9 is a diagram illustrating merging of disjoined region of a region of interest according to an example embodiment of the invention; and FIG. 10 is a flowchart for generating one or more regions of interest according to an example embodiment of the invention.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein. Like reference numerals refer to like elements throughout. As used herein, the terms "data," "content," "information" and similar terms may be used interchangeably to refer to data capable of being transmitted, received and/or stored in accordance with embodiments of the invention. Moreover, the term "example", as used herein, is not provided to convey any qualitative assessment, but instead merely to convey an illustration of an example. Thus, use of any such terms should not be taken to limit the spirit and scope of embodiments of the invention.

As defined herein a "computer-readable storage medium," which refers to a non-transitory, physical or tangible storage medium (e.g., volatile or non-volatile memory device), may be differentiated from a "computer-readable transmission medium," which refers to an electromagnetic signal.

As referred to herein, a region(s) of interest (ROI(s)) may, but need not, refer to a curved annotation (e.g., a closed curve annotation(s)) corresponding to an area(s) of one or more medical images for annotation of the medical images. The region(s) of interest may be generated based in part on one or more touch based gestures.

General System Architecture

Reference is now made to FIG. 1, which is a block diagram of a system according to example embodiments. As shown in FIG. 1, the system 2 (e.g., a health care system) may include one or more communication devices 100 (e.g., smart devices, personal computers, laptops, workstations, servers, personal digital assistants, and the like, etc.) which may access one or more network entities such as, for example, a computing device 145 (e.g., a server), or any other similar network entity, over a network 140, such as a wired local area network (LAN) or a wireless local area network (WLAN), a metropolitan network (MAN) and/or a wide area network (WAN) (e.g., the Internet). In this regard, the computing device 145 is capable of receiving data from and transmitting data to the communication devices 100 via network 140.

In one example embodiment, the communication devices 100 may be utilized by one or more clinicians, nurses, pharmacists, physicians, physical therapists and/or any other suitable health care professionals or users (e.g., a patient(s)) to communicate with the computing device 145 in order to request a medical image(s) (e.g., a Digital Imaging and Communications in Medicine (DICOM) medical image(s)). In response to receipt of the request, the computing device 145 may send the requesting communication device 100 a corresponding medical image(s). The medical image(s) received from the computing device 145, or a medical image(s) pre-stored in a memory of the communication device 100, may be utilized by the requesting communication device 100 to generate one or more regions of interest associated with the medical image(s) which may be used for annotating the medical image(s), as described more fully below.

It should be pointed out that although FIG. 1 shows six communication devices 100 and one computing device 145 any suitable number of communication devices 100 and computing devices 145 may be part of the system of FIG. 1 without departing from the spirit and scope of the invention.

Computing Device

FIG. 2 illustrates a block diagram of a computing device according to an example embodiment of the invention. The computing device 145 may, but need not, be a network entity such as, for example, a server. The computing device 145 includes various means for performing one or more functions in accordance with example embodiments of the invention, including those more particularly shown and described herein For example, as shown in FIG. 2, the computing device 145 may include a processor 34 connected to a memory 36. The memory may comprise volatile and/or non-volatile memory, and typically stores content (e.g., media content, medical images, etc.), data, information or the like.

For example, the memory may store content transmitted from the communication devices 100. In this regard, in an example embodiment, the memory 36 may store one or medical images (e.g., DICOM medical images, X-rays of the human body, etc.) and any other suitable information.

Also for example, the memory 36 typically stores client applications, instructions, algorithms or the like for execution by the processor 34 to perform steps associated with operation of the computing device 145 in accordance with embodiments of the invention. As explained below, for example, the memory 36 may store one or more client applications such as for example software (e.g., software code also referred to herein as computer code).

The processor 34 may be embodied as a controller, coprocessor, microprocessor of other processing devices including integrated circuits such as, for example, an application specific integrated circuit (ASIC), a field programmable gate array (FPGA). In an example embodiment, the processor may execute instructions stored in the memory 36 or otherwise accessible to the processor 34. The processor 34 may also be connected to at least one communication interface 38 or other means for transmitting and/or receiving data, content or the like.

The computing device 145 may also include at least one user interface that may include one or more earphones and/or speakers, a display 30, and/or a user input interface 32. The user input interface, in turn, may comprise any of a number of devices allowing the entity to receive data from a user, such as a microphone, a keypad, keyboard, a touch display, a joystick, image capture device, pointing device (e.g., mouse), stylus or other input device.

In an example embodiment, the processor 34 may receive a request for one or more medical images stored in the memory 36 from a communication device 100. In response to receipt of the request, the processor 34 may send the communication device 100 the requested medical images. The communication device 100 may utilize the received medical images, or a medical image(s) prestored in its memory 86, to generate one or more regions of interest associated with corresponding areas of the medical images. The generated regions of interest may be utilized to annotate the medical image(s), as described more fully below.

Communication Device

FIG. 3 illustrates a block diagram of a communication device according to an example embodiment of the invention. The communication device 100 includes various means for performing one or more functions in accordance with example embodiments of the invention, including those more particularly shown and described herein. It should be understood, however, that one or more of the communication devices may include alternative means for performing one or more like functions, without departing from the spirit and scope of the invention. More particularly, for example, as shown in FIG. 3, the communication device 100 may include a processor 70 connected to a memory 86. The memory may comprise volatile and/or non-volatile memory, and typically stores content (e.g., media content, medical information, etc.), data, information or the like.

For example, the memory may store content transmitted from the computing device 145 or other communication devices 100. In this regard, the memory is capable of storing data including, but not limited to, medical data such as medical images or X-rays of the human body or one or more parts of the human body, as well as any other suitable medical information. The medical images described herein may be generated with the use of non-ionizing radiation, electromagnetic energy emitted by X-rays, ultrasound technology, magnetic resonance imaging or any other suitable mechanism or modality to view anatomical parts of the human body or animals. The medical images described herein may be formatted in accordance with the DICOM protocol which is a standard for storing handling, printing, receiving and transmitting information in medical imaging.

Also for example, the memory 86 typically stores client applications, instructions, algorithms or the like for execution by the processor 70 to perform steps associated with operation of the communication device 100 in accordance with embodiments of the invention. As explained below, for example, the memory 86 may store one or more client applications such as, for example, software (e.g., software code also referred to herein as computer code).

The processor 70 may be embodied in a variety of ways. For instance, the processor 70 may be embodied as a controller, coprocessor, microprocessor of other processing devices including integrated circuits such as, for example, an application specific integrated circuit (ASIC), a field programmable gate array (FPGA). In an example embodiment, the processor may execute instructions stored in the memory 86 or otherwise accessible to the processor 70.

The communication device 100 may include one or more logic elements for performing various functions of one or more client applications. In an example embodiment, the communication device 100 may execute the client applications. The logic elements performing the functions of one or more client applications may be embodied in an integrated circuit assembly including one or more integrated circuits (e.g., an ASIC, FPGA or the like) integral or otherwise in communication with a respective network entity (e.g., computing system, client, server, etc.) or more particularly, for example, a processor 70 of the respective network entity.

In addition to the memory 86, the processor 70 may also be connected to at least one interface or other means for displaying, transmitting and/or receiving data, content or the like. The interface(s) can include at least one communication interface 88 or other means for transmitting and/or receiving data, content or the like. In this regard, the communication interface 88 may include, for example, an antenna and supporting hardware and/or software for enabling communications with a wireless communication network. For example, the communication interface(s) may include a first communication interface for connecting to a first network, and a second communication interface for connecting to a second network. In this regard, the communication device is capable of communicating with other devices such as, for example, the computing device 145 or other communication devices over one or more networks (e.g., network 140) such as a Local Area Network (LAN), wireless LAN (WLAN), Wide Area Network (WAN), Wireless Wide Area Network (WWAN), the Internet, or the like. Alternatively, the communication interface can support a wired connection with the respective network.

In addition to the communication interface(s), the interface (s) may also include at least one user interface that may include one or more earphones and/or speakers, a touch screen display 80, and/or a user input interface 82. The user input interface, in turn, may comprise any of a number of devices allowing the entity to receive data from a user, such as a microphone, a keypad, keyboard, a touch display, a joystick, image capture device, pointing device (e.g., mouse), stylus or other input device.

The touch screen display 80 may be configured to enable touch recognition by any suitable technique, such as resistive, capacitive, infrared, strain gauge, surface wave, optical imaging, dispersive signal technology, acoustic pulse recognition, or other like techniques. The touch screen display 80 may also detect finger movements just above the touch screen display even in an instance in which the finger may not actually touch the touch screen display 80. The touch screen interface 54 may be in communication with the touch screen display 80 to receive indications of user inputs at the touch screen display 80 and to modify a response to such indications based on corresponding user actions that may be inferred or otherwise determined responsive to the indications. In this regard, the touch screen interface 54 may be any device or means embodied in either hardware, software, or a combination of hardware and software configured to perform the respective functions associated with the touch screen interface 54 as described below.

In an example embodiment, the touch screen interface 54 may be embodied in software as instructions that are stored in the memory device 86 and executed by the processor 70. Alternatively, the touch screen interface 54 may be embodied as the processor 70 configured to perform the functions of the touch screen interface 54.

The touch screen interface 54 may be configured to receive one or more indications of an input in the form of a touch point or touch event at the touch screen display 80. In response to recognition of the touch event, the touch screen interface 54 may be configured to subsequently determine a stroke event or other input gesture and may provide a corresponding indication on the touch screen display 80 based on the stroke event. In this regard, for example, the touch screen interface 54 may include a detector 50 to receive indications of user inputs in order to recognize and/or determine a touch point or touch event based on each input received at the detector 50.

In an example embodiment, one or more sensors (e.g., sensor 81) may be in communication with the detector 50, via processor 70. The sensors may be any of various devices, circuitry, or modules configured to sense one or more conditions. In this regard, for example, a condition(s) that may be monitored by the sensor 81 may include pressure (e.g., an amount of pressure exerted by a touch point or touch event) and any other suitable parameters (e.g., an amount of time in which the touch screen display 80 was pressed, or a size of an area of the touch screen display 80 that was pressed).

A touch point (also referred to herein interchangeably as a touch event) may be defined as a detection of an object, such as a stylus, finger, pen, pencil or any other pointing device, coming into contact with a portion of the touch screen display 80 in a manner sufficient to register as a touch (or registering of a detection of an object just above the touch screen display 80 (e.g., hovering of a finger)). In this regard, for example, a touch event could be a detection of pressure on the screen of touch screen display 80 above a particular pressure threshold over a given area. In an alternative example embodiment, a touch point may be a detection of pressure on the screen of touch screen display 80 for longer than a particular threshold time. After each touch point, the touch screen interface 54 (e.g., via the detector 50) may be further configured to recognize and/or determine a corresponding stroke event or input gesture. A stroke event (which may also be referred to as an input gesture) may be defined as a touch point followed immediately by motion of the object initiating the touch point while the object remains in contact with the touch screen display 80. In other words, the stroke event or input gesture may be defined by motion following a touch point thereby forming a continuous, moving touch point defining a moving series of instantaneous touch positions. The stroke event or input gesture may represent a series of unbroken touch points, or in some cases a combination of separate touch points. With respect to the description above, the term "immediately" should not necessarily be understood to correspond to a temporal limitation. Rather, the term "immediately," while it may generally correspond to a relatively short time after a touch event in many instances, instead is indicative of no intervening actions between the touch event and the motion of the object defining the touch positions while such object remains in contact with the touch screen display 80. In this regard, it should be pointed out that no intervening actions may cause operation or function of the touch screen. However, in some instances in which a touch point that is held for a threshold period of time triggers a corresponding function, the term immediately may also have a temporal component associated in that the motion of the object causing the touch point must occur before the expiration of the threshold period of time.

In an example embodiment, the detector 50 may be configured to communicate detection information regarding the recognition or detection of a stroke event or input gesture as well as a selection of one or more items of data (e.g., images (e.g., medical images), text, graphical elements, etc.) to a data analyzer 62. The data analyzer 62 may, in turn, communicate with a region of interest module 78. In one embodiment, the data analyzer 62 (along with the detector 50) may be a portion of the touch screen interface 54. In an example embodiment, the touch screen interface 54 may be embodied by a processor, controller of the like. In addition, the data analyzer 62 and the detector 50 may each be embodied as any means such as a device or circuitry embodied in hardware, software or a combination of hardware and software that is configured to perform corresponding functions of the data analyzer 62 and the detector 50, respectively.

In an example embodiment, the processor 70 may be in communication with and may otherwise control a region of interest module 78 (also referred to herein as a ROI module 78). The region of interest module 78 may be any means such as a device or circuitry operating in accordance with software or otherwise embodied in hardware or a combination of hardware and software thereby configuring the device or circuitry (e.g., a processor, controller, microprocessor or the like) to perform the corresponding functions of the region of interest module 78, as described below. In examples in which software is employed, a device or circuitry (e.g., processor 70 in one example) executing the software forms the structure associated with such means. As such, for example, the region of interest module 78 may be configured to, among other things, generate one or more free form annotations (e.g., closed curve annotations) defining a region(s) of interest associated with corresponding areas of one or more medical images. The region(s) of interest may be generated based in part on one or more touch-based gestures, as described more fully below.

Example System Operation

Example embodiments of the invention may provide an efficient and reliable mechanism for generating one or more annotations (e.g., closed curve annotations) using touch-based gestures to define one of more regions of interest for one or more corresponding medical images. In this regard, an example embodiment may provide an efficient and intuitive manner in which to generate and modify annotations (e.g., closed curve annotations) defining regions of interest for medical images via devices utilizing touch-based technology.

In an example embodiment, an annotation(s) may be utilized to define a region(s) of interest (ROI). The ROI may be utilized by a user to identify one or more relevant features of interest within a medical image(s) (e.g., a tumor). In this regard, an example embodiment may, for example, use the identified region of interest to compute and display to the user specific measurement data pertinent to a clinical scenario or any other suitable data associated with the medical image. For purposes of illustration and not of limitation, the measurement data may include, but is not limited to, average density, an ROI area, an ROI perimeter, and any other suitable measurement data.

As examples in which the ROI module 78 may generate or modify one or more regions of interest, consider FIGS. 4-9 described more fully below for purposes of illustration and not of limitation. It should be pointed out that the regions of interest associated with FIGS. 4-9 may relate to an area(s) of interest at one or more respective medical images. The medical images may be prestored in a memory (e.g., memory 86) of a communication device 100 or may be received from the computing device 145 or one or more other communications devices 100. Additionally, the generated regions of interest may be overlaid on corresponding areas of one or more medical images on a touch enabled display (e.g., touch screen display 80).

Referring now to FIG. 4, a diagram illustrating creation of a region of interest associated with a medical image(s) according to an example embodiment is provided. A region of interest may be generated by the ROI module 78 in response to receipt of an indication of a touch at the touch screen display 80 of the communication device 100. In this regard, in an instance in which the ROI module 78 receives an indication of a touch at the touch screen display 80, the ROI module 78 may generate a ROI 3 (e.g., a circular ROI) of a predetermined size at a location corresponding to the detected touch. The diameter D of the generated ROI 3 may be configured to be approximately equal to the width of an adult human index finger (e.g., D=1.8 cm). In this manner, a contour(s) of the generated ROI may be defined by a virtual disc of diameter D.

In an alternative example embodiment, the ROI module 78 may utilize the sensor 81 to measure an amount of pressure of one or more touches at the touch screen display 80 in order to generate the diameter D. As such, the ROI module 78 may be utilized to define the diameter D of the virtual disc by calculating diameter D as a function of the measured pressure associated with a respective touch point(s). For example, the ROI module 78 may determine that diameter D may vary linearly between a minimum predefined value m and a maximum predefined value M according to the formula D=m+(M−m)*p, where p is the amount of measured pressure at the touch point(s) and is normalized to the interval [0,1] (e.g., any value between 0 and 1 may be included). In this regard, the ROI module 78 may determine that the diameter D may thus vary continuously as the pressure changes during detection of one or more touches.

In addition, the ROI module 78 may generate multiple ROIs in response to receipt of an indication of multiple touches of corresponding fingers at the touch screen display 80. In this regard, the contour of a corresponding ROI(s) may be defined by a virtual elastic band surrounding corresponding virtual discs of diameter D located at each touch point, for example, at each point that one or more fingers touch the touch screen display 80. A portion of a generated ROI may be modified in response to an indication of a contour(s) of the ROI being overlapped or traversed by a finger being moved across the touch screen display 80.

As described more fully below, according to an example embodiment, the ROI module 78 may expand an ROI, shrink or remove a portion of an ROI, or otherwise modify an ROI by determining that one or more respective touch points (e.g., touches of a finger(s)) detected at the touch screen display 80 define one or more corresponding virtual discs that follow or track the movement of the touch points. In this regard, the ROI module 78 may determine that for each change in a position of a corresponding virtual disc(s) that overlaps a contour of a ROI, the section of the contour that overlaps the corresponding virtual disc(s) may be modified by the ROI module 78 so that it follows the edge of the corresponding virtual disc(s). By modifying an a section of a contour of an ROI such that it follows the edge of the corresponding virtual disc(s), the ROI module 78 may expand, shrink, remove or otherwise modify an ROI, as described more fully below.

Referring now to FIGS. 5 & 6, diagrams illustrating a manner of expanding a generated ROI associated with a medical image(s) according to an example embodiment are provided. As shown in FIG. 5, the ROI module 78 may expand or grow a generated ROI (e.g., ROI 3) to obtain an expanded ROI 5 in response to receipt of an indication of a touch of a finger (or similar actuating entity, such as a stylus) at the touch screen display 80 and in response to receipt of an indication that the finger is being dragged or moved across the touch screen display without being lifted from the touch screen display 80, for example. Additionally, the ROI module 78 may expand an existing or generated ROI (e.g., ROI 3) in response to receipt of an indication of a touch of a finger (or similar actuating entity) inside of the generated ROI and detection of the finger being dragging across the touch screen display 80. For instance, as shown in FIG. 6, the ROI module 78 may expand a generated ROI (e.g., ROI 3) in response to receipt of an indication of a touch of a finger inside the generated ROI and detection of the finger being dragged or moved across the touch screen display 80 along a path 7 defining a contour 9 of the expanded ROI 11.

It should be pointed out that in one example embodiment of FIG. 6, the ROI 3 may be expanded by the ROI module 78 to form the expanded ROI 11 in response to the ROI module 78 receiving an indication that a contour of a generated ROI (e.g., ROI 3) is being overlapped or traversed such that the disc of the generated ROI (e.g., ROI 3) follows the disc edge, which may modify the generated ROI (e.g., ROI 3) to create the expanded ROI 11.

Referring now to FIG. 7, a diagram illustrating a manner of shrinking or removing a region of interest associated with a medical image(s) according to an example embodiment is provided. In this regard, the ROI module 78 may shrink a ROI, in response to receipt of an indication, by the ROI module 78, of a detection of one or more touches of a finger outside of a generated ROI and an indication that the finger is dragged across a portion of the ROI. For example, as shown in the example embodiment of FIG. 7, in response to receipt of an indication of a detection of a touch of a finger outside of the ROI 12 and that the finger is being dragged or moved across the touch screen display 80 over a corresponding portion 14 of the ROI 12, the ROI module 78 may shrink or remove the corresponding portion 14 from the ROI. More particularly, for the example embodiment in FIG. 7, the ROI module 78 may remove the portion 14 of the ROI 12 in response to detection of the indication of the finger outside of the ROI 12 and detection of the finger being moved across or within a portion of the ROI 12 such that the finger overlaps or traverses at least one contour 8 of the ROI 12. In this regard, by removing the corresponding portion 14, the ROI module 78 may delete the corresponding portion 14 of the ROI 12.

As another example, consider an instance in which the ROI module 78 may detect a touch of a finger outside of an upper area of the ROI 12 and a detection of the finger being dragged across the touch screen display 80 corresponding to a center portion of the ROI 12. Consider further that the ROI module 78 then detects that the finger is lifted from the touch screen display 80. In this example, the ROI module 78 may remove the portion of the ROI 12 that the finger was dragged across and the other portions of the ROI 12 may remain intact.

In an example embodiment, the ROI module 78 may expand and/or remove one or more portions of a generated region of interest simultaneously. For example, the ROI module 78 may simultaneously remove and expand corresponding portions of a generated ROI in response to receipt of a detection of a touch of at least one finger outside of the ROI being dragged across the touch screen display 80 to a corresponding portion inside the ROI, which removes the corresponding portion of the ROI and detection of at least one other finger inside the ROI being dragged across the touch screen display 80 to an outer edge of the ROI such that a contour of the ROI is overlapped and moved outwardly, which expands the ROI.

As described above, according to embodiments of the present invention, the ROI module 78 may expand an ROI, shrink or remove a portion of an ROI or otherwise modify an ROI by determining that one or more respective touch points (e.g., touch of a finger) detected at the touch screen display 80 define one or more corresponding virtual discs and that the virtual discs follow or track the movement of the touch points.

In this regard, the ROI module 78 may determine that for every change in a position of a corresponding virtual disc(s) that overlaps a contour of a ROI, the section of the contour that overlaps the corresponding virtual disc(s) is modified by the ROI module 78 so that it follows the edge of the corresponding virtual disc(s).

Referring now to FIG. 8, a diagram illustrating a manner in which to disjoin a region of interest associated with medical image(s) according to an example embodiment is provided. In the example embodiment of FIG. 8, the ROI module 78 may generate the ROI 15. The ROI module 78 may disjoin the ROI 15 of the example embodiment of FIG. 8. For example, the ROI module 78 may split the ROI 15 in response to an indication of a detection of a touch of a finger on the touch screen display 80 outside of the ROI 15 and detection of the finger being dragged through the ROI 15 such that a contour 21 of the ROI 15 is being moved, by a virtual disc associated with the finger, to reach a lower contour section 23 of the ROI 15. In the example of FIG. 8, the ROI 15 may become disjoint, by the ROI module 78, as soon as the removal of the overlapping contour sections 21 and 23 result in two separate closed curves 25 and 27. In this manner, the ROI module 78 may interactively modify the ROI 15 as the finger is being dragged as opposed to modification at the end of the touch interaction with the touch screen display 80. As such, the ROI module 78 may split the ROI 15 into two disjoint regions 17 and 19, as defined by the resulting closed curves 25 and 27. The disjoint regions 17 and 19 may be expanded and portions of the disjoint regions 17 and 19 may be removed by the ROI module 78, in a manner analogous to that described above.

In one example embodiment, the disjoint regions 17 and 19 may remain united and form the same ROI 15 from which they were split, even though they are physically separated. In other words, although the disjoint regions 17 and 19 are physically separated, they may remain part of the ROI 15 and the data associated with respective portions of a medical images(s) corresponding to disjoint regions 17 and 19 may remain united. As such, for example, in an instance in which an average density measurement may be computed for the ROI 15, the average density measurement may correspond to the union of the two resulting regions 17 and 19 to yield one measurement as opposed to two separate average density measurements corresponding to each of the disjointed regions 17 and 19.

In an alternative example embodiment, splitting of the ROI 15, by the ROI module 78, may result in the generation of two disjointed regions 17 and 19 that may relate to two different ROIs and as such the disjointed regions 17 and 19 may no longer be united. In this alternative embodiment, the data associated with respective portions of a medical images(s) corresponding to disjoint regions 17 and 19 may no longer be united. As such, for example, an average density measurement computed for disjointed regions 17 and 19 may result in two separate and distinct measurements corresponding to each of the disjointed regions 17 and 19.

Referring now to FIG. 9, a diagram illustrating a manner in which to reconnect disjoined regions of a region of interest associated with a medical image(s) according to an example embodiment is provided. As shown in FIG. 9, the ROI module 78 may reconnect the disjoined regions 17 and 19 in response to the ROI module 78 enabling the contours 29 and 31 associated with curves 25, 27 (See e.g., FIG. 8) to overlap. The ROI module 78 may enable the contours 29 and 31 to overlap in response to receipt of an indication of a detection of a touch of a finger inside disjoined region 17 and an indication of a detection of the finger being dragged across the touch screen display 80 to an edge of the contour 31 of the disjoined region 19. In this regard, the overlapping contour sections 29 and 31 may be removed by the ROI module 78 and the ROI module 78 may fuse or merge the disjoined regions 17 and 19 to form ROI 15. In other words, the ROI module 78 may detect the touch of a finger across display 80 as the finger is being dragged, and an associated virtual disc, generated by the ROI module 78, may push the contour 29 of the disjoined region 17 outwards. As the contour 29 is pushed towards the disjoined region 19, by the associated virtual disc, the contour sections may be overlapped and removed and as such the two disjoined regions 17 and 19 may be merged to form ROI 15 in the manner in which ROI 15 was originally generated by the ROI module 78.

It should be pointed out that the ROI module 78 may allow other interactions with the generated ROIs. For instance, in response to receipt of an indication of a touch of a generated ROI on the touch screen display 80, the ROI module 78 may toggle control annotation control points or widgets that may allow scaling, rotating, skewing, other transformations of the corresponding ROI, deleting the corresponding ROI and any other suitable interactions.

Referring now to FIG. 10, a flowchart for generating one or more annotations (e.g., closed curve annotations) for defining a region(s) of interest associated with a medical image(s) according to an example embodiment is provided. At operation 1000, an apparatus (e.g., ROI module 78) may receive an indication of one or more touches at corresponding locations on a touch enabled display. The touches may define a touch point at the corresponding location. At operation 1005, an apparatus (e.g., ROI module 78) may generate one or more regions of interest (e.g., ROI 5) associated with one or more areas of a medical image(s) in response to receipt of the indications of the touches. The location of the regions of interest corresponds to locations of respective touch points. At operation 1010, the apparatus (e.g., ROI module 78) may define a diameter (e.g., D=1.8 cm) of the regions of interest based in part on a width or an amount of pressure of the corresponding touch points. At operation 1015, an apparatus (e.g., ROI module 78) may define each of the regions of interest to include at least one disc including one or more contours. The respective regions of interest may correspond to an area for annotating the medical image.

It should be pointed out that FIG. 10 is a flowchart of a system, method and computer program product according to example embodiments of the invention. It will be understood that each block or step of the flowchart, and combinations of blocks in the flowchart, can be implemented by various means, such as hardware, firmware, and/or a computer program product including one or more computer program instructions. For example, one or more of the procedures described above may be embodied by computer program instructions. In this regard, in an example embodiment, the computer program instructions which embody the procedures described above are stored by a memory device (e.g., memory 86, memory 36) and executed by a processor (e.g., processor 70, processor 34, region of interest module 78). As will be appreciated, any such computer program instructions may be loaded onto a computer or other programmable apparatus (e.g., hardware) to produce a machine, such that the instructions which execute on the computer or other programmable apparatus cause the functions specified in the flowchart blocks or steps to be implemented. In some embodiments, the computer program instructions are stored in a computer-readable memory that can direct a computer or other programmable apparatus to function in a particular manner, such that the instructions stored in the computer-readable memory produce an article of manufacture including instructions which implement the function specified in the flowchart blocks or steps. The computer program instructions may also be loaded onto a computer or other programmable apparatus to cause a series of operational steps to be performed on the computer or other programmable apparatus to produce a computer-implemented process such that the instructions which execute on the computer or other programmable apparatus provide steps for implementing the functions specified in the flowchart blocks or steps.

Accordingly, blocks or steps of the flowchart support combinations of means for performing the specified functions and combinations of steps for performing the specified functions. It will also be understood that one or more blocks or steps of the flowchart, and combinations of blocks or steps in the flowchart, can be implemented by special purpose hardware-based computer systems which perform the specified functions or steps, or combinations of special purpose hardware and computer instructions.

In an example embodiment, an apparatus for performing the methods of FIG. 10 above may comprise a processor (e.g., the processor 70, the processor 34, the region of interest module 78) configured to perform some or each of the operations described above. The processor may, for example, be configured to perform the operations by performing hardware implemented logical functions, executing stored instructions, or executing algorithms for performing each of the operations. Alternatively, the apparatus may comprise means for performing each of the operations described above. In this regard, according to an example embodiment, examples of means for performing operations may comprise, for example, the processor 34, the processor 70 (e.g., as means for performing any of the operations described above), the region of interest module 78 and/or a device or circuit for executing instructions or executing an algorithm for processing information as described above.

CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method comprising:
   receiving an indication of one or more touches at a corresponding one or more locations on a touch enabled display, respective touches defining a touch point at the corresponding location;
   generating, via a processor, one or more regions of interest associated with one or more areas of at least one medical image in response to receipt of the one or more indications, a location of respective regions of interest corresponding to the location of respective one or more touch points;
   defining a diameter of respective regions of interest based in part on a width or an amount of pressure of the corresponding touch points at the corresponding locations on the touch enabled display;
   defining each of the regions of interest to comprise at least one disc comprising the diameter and one or more contours, wherein the respective regions of interest correspond to an area for annotating the medical image; and
   disjoining at least one of the regions of interest in response to receipt of an indication of a first touch point, of the touch points, outside of an area of the at least one region of interest being moved across the touch enabled display to traverse a first contour and a second contour of the region of interest,
   wherein disjoining comprises splitting the at least one region of interest into two disjoined regions.

2. The method of claim 1, wherein the regions of interest are overlaid on corresponding areas of the medical image displayed via the touch enabled display.

3. The method of claim 1, further comprising:
   expanding a size of at least one of the regions of interest in response to receipt of an indication of a detection of a first touch point, of the touch points, being moved across the touch enabled display or in response to receipt of an indication of at least one second touch point, of the touch points, within the at least one region of interest being moved across the touch enabled display in an outward direction overlapping a first contour of the region of interest.

4. The method of claim 1, further comprising:
   removing a portion of at least one of the regions of interest in response to receipt of a detection of an indication of a first touch point, of the touch points, outside of an area of the at least one region of interest and in response to receipt of an indication that the first touch point is being moved across the touch enabled display within at least a portion of the region of interest and overlaps a first contour of the region of interest.

5. The method of claim 1, comprising:
   enabling the two disjoined regions to remain united, even though the two disjoined regions are separated by uniting the data associated with the two disjoined regions.

6. The method of claim 5, wherein uniting the data comprises uniting the data of the medical image.

7. The method of claim 1, wherein splitting the at least one region of interest into two disjoined regions comprises generating a first region of interest associated with a first disjoined region of the two disjoined regions and a second region of interest associated with a second disjoined region of the two disjoined regions and the method further comprises:
   determining that the data associated with the two disjoined regions are no longer united.

8. The method of claim 1, further comprising:
   merging the two disjoined regions to obtain the at least one region of interest in response to receipt of an indication of a second touch point, of the touch points, inside a first disjoined region of the two disjoined regions being moved across the touch enabled device to overlap a contour of the first disjoined region and to overlap a contour of the second disjoined region of the two disjoined regions.

9. The method of claim 1, further comprising:
   modifying at least one of the generated regions of interest in response to detection of an indication of a contour of the region of interest being overlapped or traversed by a touch point being moved across the touch enabled display.

10. The method of claim 1, wherein:
generating the one or more regions of interest further comprises generating the one or more regions of interest comprising a predetermined size in response to the receipt of the indications.

11. An apparatus comprising:
at least one processor; and
at least one memory including computer program code, the at least one memory and the computer program code configured to, with the at least one processor, cause the apparatus to perform at least the following:
receive an indication of one or more touches at a corresponding one or more locations on a touch enabled display, respective touches defining a touch point at the corresponding location;
generate one or more regions of interest associated with one or more areas of at least one medical image in response to receipt of the one or more indications, a location of respective regions of interest corresponding to the location of respective one or more touch points;
define a diameter of respective regions of interest based in part on a width or an amount of pressure of the corresponding touch points at the corresponding locations on the touch enabled display;
define each of the regions of interest to comprise at least one disc comprising the diameter and one or more contours, wherein the respective regions of interest correspond to an area for annotating the medical image; and
disjoin at least one of the regions of interest in response to receipt of an indication of a first touch point, of the touch points, outside of an area of the at least one region of interest being moved across the touch enabled display to traverse a first contour and a second contour of the region of interest,
wherein disjoin the at least one region comprises splitting the at least one region of interest into two disjoined regions.

12. The apparatus of claim 11, wherein the at least one memory and the computer program code are further configured to, with the at least one processor, cause the apparatus to:
overlay the regions of interest on corresponding areas of the medical image displayed via the touch enabled display.

13. The apparatus of claim 11, wherein the at least one memory and the computer program code are further configured to, with the at least one processor, cause the apparatus to:
expand a size of at least one of the regions of interest in response to receipt of an indication of a detection of a first touch point, of the touch points, being moved across the touch enabled display or in response to receipt of an indication of at least one second touch point, of the touch points, within the at least one region of interest being moved across the touch enabled display in an outward direction overlapping a first contour of the region of interest.

14. The apparatus of claim 11, wherein the at least one memory and the computer program code are further configured to, with the at least one processor, cause the apparatus to:
remove a portion of at least one of the regions of interest in response to receipt of a detection of an indication of a first touch point, of the touch points, outside of an area of the at least one region of interest and in response to receipt of an indication that the first touch point is being moved across the touch enabled display within at least a portion of the region of interest and overlaps a first contour of the region of interest.

15. The apparatus of claim 11, wherein the at least one memory and the computer program code are further configured to, with the at least one processor, cause the apparatus to:
enable the two disjoined regions to remain united, even though the two disjoined regions are separated by uniting the data associated with the two disjoined regions.

16. The apparatus of claim 15, wherein the at least one memory and the computer program code are further configured to, with the at least one processor, cause the apparatus to:
unite the data by uniting the data of the medical image.

17. The apparatus of claim 11, wherein the at least one memory and the computer program code are further configured to, with the at least one processor, cause the apparatus to:
split the at least one region of interest into two disjoined regions by generating a first region of interest associated with a first disjoined region of the two disjoined regions and a second region of interest associated with a second disjoined region of the two disjoined regions; and
determine that the data associated with the two disjoined regions are no longer united.

18. The apparatus of claim 11, wherein the at least one memory and the computer program code are further configured to, with the at least one processor, cause the apparatus to:
merge the two disjoined regions to obtain the region of interest in response to receipt of an indication of a second touch point, of the touch points, inside a first disjoined region of the two disjoined regions being moved across the touch enabled device to overlap a contour of the first disjoined region and to overlap a contour of the second disjoined region of the two disjoined regions.

19. The apparatus of claim 11, wherein the at least one memory and the computer program code are further configured to, with the at least one processor, cause the apparatus to:
modify at least one of the generated regions of interest in response to detection of an indication of a contour of the region of interest being overlapped or traversed by a touch point being moved across the touch enabled display.

20. The apparatus of claim 11, wherein the at least one memory and the computer program code are further configured to, with the at least one processor, cause the apparatus to:
generate the one or more regions of interest by generating the one or more regions of interest comprising a predetermined size in response to the receipt of the indications.

21. A computer program product comprising at least one non-transitory computer-readable storage medium having computer-executable program code instructions stored therein, the computer executable program code instructions comprising:
program code instructions configured to facilitate receipt of an indication of one or more touches at a corresponding one or more locations on a touch enabled display, respective touches defining a touch point at the corresponding location;
program code instructions configured to generate one or more regions of interest associated with one or more areas of at least one medical image in response to receipt of the one or more indications, a location of respective regions of interest corresponding to the location of respective one or more touch points;
program code instructions configured to define a diameter of respective regions of interest based in part on a width or an amount of pressure of the corresponding touch points at the corresponding locations on the touch enabled display;

program code instructions configured to define each of the regions of interest to comprise at least one disc comprising the diameter and one or more contours, wherein the respective regions of interest correspond to an area for annotating the medical image; and program code instructions configured to disjoin at least one of the regions of interest in response to receipt of an indication of a first touch point, of the touch points, outside of an area of the at least one region of interest being moved across the touch enabled display to traverse a first contour and a second contour of the region of interest, wherein disjoin the at least one region comprises splitting the at least one region of interest into two disjoined regions.

22. The computer program product of claim 21, further comprising:

program code instructions configured to expand a size of at least one of the regions of interest in response to receipt of an indication of a detection of a first touch point, of the touch points, being moved across the touch enabled display or in response to receipt of an indication of at least one second touch point, of the touch points, within the at least one region of interest being moved across the touch enabled display in an outward direction overlapping a first contour of the region of interest.

23. The computer program product of claim 21, further comprising:

program code instructions configured to modify at least one of the generated regions of interest in response to detection of an indication of a contour of the region of interest being overlapped or traversed by a touch point being moved across the touch enabled display.

24. The computer program product of claim 21, wherein:

generate the one or more regions of interest further comprises generating the one or more regions of interest comprising a predetermined size in response to the receipt of the indications.

* * * * *